United States Patent [19]

Quinn et al.

[11] 4,240,968
[45] Dec. 23, 1980

[54] PROCESS FOR ISOLATING AND PURIFYING DIPHENOL BY-PRODUCTS

[75] Inventors: Clayton B. Quinn; Clayton W. Reinitz; William Hilakos, all of Mt. Vernon, Ind.

[73] Assignee: General Electric Company, Pittsfield, Mass.

[21] Appl. No.: 33,392

[22] Filed: Apr. 26, 1979

[51] Int. Cl.³ .......................................... C07D 311/04
[52] U.S. Cl. ................................. 260/345.2; 568/724
[58] Field of Search .................... 568/724; 260/345.2

[56] References Cited

U.S. PATENT DOCUMENTS

| 2,845,464 | 7/1958 | Luten, Jr. ............................. 568/724 |
| 3,073,868 | 1/1963 | Prahl et al. ........................... 568/724 |
| 3,207,795 | 9/1965 | Prahl et al. ........................... 568/724 |
| 4,156,098 | 5/1979 | Li ......................................... 568/724 |

Primary Examiner—Nicky Chan
Attorney, Agent, or Firm—William F. Mufatti

[57] ABSTRACT

A process is disclosed for isolating and purifying diphenol by-products to obtain an enriched chroman-I concentrate. The process includes slurrying a mixture of diphenol by-products in a suitable solvent system to form a solid, and then recovering, washing and drying the collected solid.

15 Claims, No Drawings

PROCESS FOR ISOLATING AND PURIFYING DIPHENOL BY-PRODUCTS

This invention is directed toward a process for isolating and purifying diphenol by-products and to high molecular weight aromatic polycarbonates obtained employing the isolated and purified diphenol by-products.

BACKGROUND OF THE INVENTION

High molecular weight aromatic polycarbonate resins are generally obtained from an interfacial or phase boundry process or by means of interesterification or by a combination of both processes. Such processes are disclosed in U.S. Pat. No. 3,028,365.

In these processes, diphenol is employed as one of the major reactants and is either supplied to the polycarbonate manufacturer or produced by him at his plant site. In the latter instance, the crude diphenol, prior to use, is distilled and then recrystallized in a suitable solvent. The solvent is then filtered and crystalline diphenol is collected. The material which does not crystallize and which remains with the filtrate is concentrated in a solvent stripper. The concentrated material is dark colored and, in addition to containing diphenol, also contains a large portion of diphenol by-products. Although diphenol by-products can be employed to produce high molecular weight aromatic polycarbonate resins, the polycarbonate resins obtained are also dark colored and of inferior quality.

Some of the by-products contained in the diphenol can be used efficiently and effectively in the production of polycarbonate resins. For example, chroman which is typically found in such by-products, can be used as a molecular weight regulator or chain stopper in producing high molecular weight aromatic polycarbonates as disclosed in U.S. Pat. No. 3,697,481.

The isolation of these by-products can, therefore, be advantageous, but they must be obtained in sufficient quantity and purity for use and the process employed should be economical if it is to be practical. U.S. Pat. No. 3,825,562 discloses an aqueous process for purifying such by-products employing sodium hydroxide. However, this process is not practical as it is time consuming and the relative quantity of purified by-products obtained, e.g., chroman, is not sufficient from a practical, manufacturing view point.

DESCRIPTION OF THE INVENTION

It has now been found that the by-products in a diphenol/by-product stream can be effectively, efficiently and economically isolated and purified in sufficient quantity for use in the manufacture of high molecular weight aromatic polycarbonate resins. This is accomplished by the process of the invention which, in general, comprises slurrying the diphenol by-products in a suitable solvent system until the formation of crystals is complete; collecting the resultant solid formed therefrom; washing the collected solids with fresh solvent to form a white powder; and drying the white powder. Alternatively, a suitable solvent system can first be charged to a reactor vessel; the diphenol by-products in molten form can then be added to the reactor while maintaining the solvent at constant reflux; cooling the resultant mixture to room temperature; and collecting the solids formed.

The diphenol/by-products stream contains different impurities as well as small amounts of tarry products. When the diphenol produced is 2,2'-bis(4-hydroxyphenyl)propane; i.e., bisphenol-A, hereinafter referred to as BPA, these impurities typically include the following compounds:

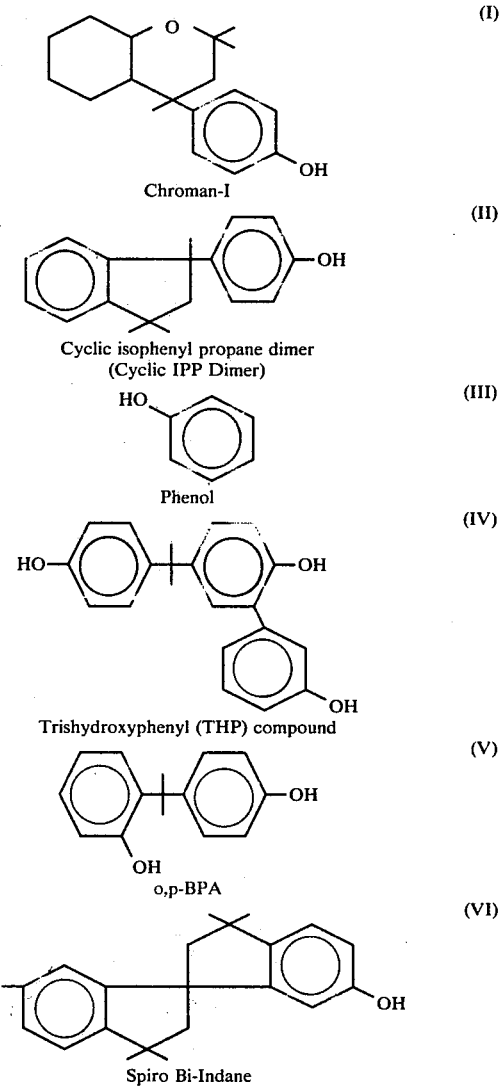

Chroman-I (I)

Cyclic isophenyl propane dimer (Cyclic IPP Dimer) (II)

Phenol (III)

Trishydroxyphenyl (THP) compound (IV)

o,p-BPA (V)

Spiro Bi-Indane (VI)

Upon isolation and purification of the diphenol by-products employing the process of the invention, the concentrations of the diphenol; e.g., BPA, and chroman-I are significantly increased, the concentration of the cyclic IPP dimer is reduced, and the remaining, undesirable components are either removed or their concentrations reduced to insignificant quantities. Thus, in addition to the particular diphenol employed, chroman-I is the primary component that is isolated and purified and which can then be readily employed as the chain stopper in the production of high molecular weight aromatic polycarbonates.

The high molecular weight aromatic polycarbonates that can be obtained in the practice of this invention are homopolymers and copolymers and mixtures thereof which have an I.V. of 0.40–1.0 dl/g as measured in methylene chloride at 25° C. which can generally be prepared by reacting a diphenol with a carbonate precursor employing the interfacial and/or interesterification processes mentioned hereinabove.

The diphenols that are typically employed to produce these polycarbonates are bisphenols such as bis(4-hydroxyphenyl)methane, 2,2-bis(4-hydroxyphenyl)propane (BPA), 2,2-bis(4-hydroxy-3-methylphenyl)propane, 4,4-bis(4-hydroxyphenyl)heptane, 2,2-bis(4-hydroxy-3,5-dichlorophenyl)propane, 2,2-bis(4-hydroxy-3,5-dibromophenyl) propane, etc.; diphenol ethers such as bis(4-hydroxyphenyl)ether, bis(3,5-dichloro-4-hydroxyphenyl)ether, etc.; dihydroxydiphenyls such as p,p'-dihydroxydiphenyl, 3,3'-dichloro-4,4-dihydroxydiphenyl, etc.; dihydroxyaryl sulfones such as bis(4-hydroxyphenyl)sulfone, bis(3,5-dimethyl-4-hydroxyphenyl)sulfone, etc.; dihydroxy benzenes, resorcinol, hydroquinone, halo- and alkyl-substituted dihydroxy benzenes such as 1,4-dihydroxy-2,5-dichlorobenzene, 1,4-dihydroxy-3-methylbenzene, etc.; and dihydroxy diphenyl sulfoxides such as bis(4-hydroxyphenyl)sulfoxide, bis(3,5-dibromo-4-hydroxyphenyl)sulfoxide, etc. A variety of additional diphenols are also available such as are disclosed in U.S. Pat. Nos. 2,999,835, 3,028,365 and 3,153,008. Also suitable are copolymers prepared from the above diphenols copolymerized with halogen-containing diphenols such as 2,2-bis(3,5-dichloro-4-hydroxyphenyl)propane, 2,2-bis(3,5-dibromo-4-hydroxyphenyl)propane, etc. It is also possible to employ two or more different diphenols or a copolymer of a diphenol with a glycol or with a hydroxy or acid terminated polyester, or with a dibasic acid as well as blends of any of the above materials.

The production of high molecular weight aromatic polycarbonate resins typically includes the use of an acid acceptor, a carbonate precursor, a catalyst and a molecular weight regulator; i.e., a chain stopper.

The acid acceptor that can be employed can be either an organic or an inorganic acid acceptor. A suitable organic acid acceptor is a tertiary amine and includes such materials as pyridine, triethylamine, dimethylaniline, tributylamine, etc. The inorganic acid acceptor can be one which can be either a hydroxide, a carbonate, a bicarbonate, or a phosphate of an alkali or alkaline earth metal.

The carbonate precursor employed can be either a carbonyl halide, a carbonate ester or a haloformate. The carbonyl halides which can be employed are carbonyl bromide, carbonyl chloride and mixtures thereof. Typical of the carbonate esters that can be employed are diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonate such as di-(tolyl) carbonate, etc., di-(naphthyl) carbonate, di(-chloronaphthyl) carbonate, phenyl tolyl carbonate, chlorophenyl chloronaphthyl carbonate, etc., or mixtures thereof. The haloformates suitable for use herein include bishaloformates of dihydric phenols (bischloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid. These are disclosed in U.S. Pat. No. 3,169,121 which is incorporated herein by reference.

The catalysts which can be employed can be any of the suitable catalysts that aid the polymerization of the bisphenol-A (BPA) and the acid dichloride with phosgene. Suitable catalysts include tertiary amines such as triethylamine, tripropylamine, N,N-dimethylaniline, quaternary ammonium compounds such as tetraethylammonium bromide, cetyl triethylammonium bromide, tetra-n-heptylammonium iodide, tetra-n-propylammonium bromide, tetramethylammonium chloride, tetra-methylammonium hydroxide, tetra-n-butylammonium iodide, benzyl-trimethylammonium chloride and quaternary phosphonium compounds such as n-butyl-triphenyl phosphonium bromide and methyl-triphenyl phosphonium bromide.

In prior art processes, the chain stoppers typically employed include monohydric phenols such as phenol, paratertiarybutylphenol, parabromophenol, primary and secondary amines, and the like, with phenol being the generally preferred chain stopper.

In the practice of this invention, the chain stopper employed is the concentrated by-products mixture obtained from the isolation and purification of the diphenol/by-products stream. As described above, this concentrated mixture mainly comprises chroman-I, along with cyclic IPP dimer and the diphenol produced and is, therefore, hereinafter referred to as "chroman-I concentrate".

To obtain the chroman-I concentrate of the invention, purification and isolation of the diphenol by-products involves the use of a suitable solvent system. The solvent system employed is one in which the diphenol/by-products stream will be accepted but which will be inert with respect to the components of the stream. For example, an aqueous organic solvent system can be employed wherein the organic member can readily accept the components, but be inert to them. Exemplary of such organic members are methylene chloride, chlorobenzene, cyclohexanone, carbon tetrachloride, and the like, as well as mixtures thereof. Preferably, the organic portion of the solvent system is methylene chloride. The amount of the organic portion of the solvent system employed, based upon the unpurified diphenol/by-products stream, can be within the range of about 1:0.5–3.0, preferably 1:1, on a weight basis of unpurified diphenol by-products:organic portion of the solvent system.

Included within the scope of this invention are branched polycarbonates wherein a polyfunctional aromatic compound is reacted with the diphenol, carbonate precursor and chroman-I concentrate to provide a thermoplastic randomly branched polycarbonate.

These polyfunctional aromatic compounds contain at least three functional groups which are carboxyl, carboxylic anhydride, haloformyl or mixtures thereof. Exemplary of the polyfunctional aromatic compounds which can be employed are trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride and the like. The preferred polyfunctional aromatic compounds are trimellitic anhydride or trimellitic acid or their haloformyl derivatives. Also included herein are blends of a linear polycarbonate and a branched polycarbonate.

PREFERRED EMBODIMENT OF THE INVENTION

Details of the invention will become more apparent from a consideration of the following examples which are set forth to illustrate the best mode currently known to practice the invention. In the examples parts and percentages are by weight unless otherwise stated.

EXAMPLE 1

A mixture of unpurified BPA by-products were collected in a molten state in 25 lb. lots from a BPA manufacturing facility. The BPA by-products were kept in a molten state in heated vessels using electrical tape. To a 25 gallon vessel equipped with an agitator and reflux condenser there was added one of the 25 lb. lots of BPA by-products. The vessel was sealed and 25 lbs. of methylene chloride as solvent was poured slowly down the reflux condenser while agitating the BPA by-products mixture. Upon completing the addition of the methylene chloride, the mixture was refluxed with agitation for about 15 minutes, whereupon agitation of the mixture was continued for about another 45 minutes without external heating. At the end of this time, the resultant slurry was poured into a basket centrifuge and the centrifuge cake obtained was spray washed with fresh, undiluted methylene chloride. About 7 lbs. of the chroman-I concentrate in the form of a white solid were collected, dried in an air oven at 100° C. and mechanically blended to insure homogeneity.

The unpurified BPA by-products and the chroman-I concentrate were analyzed using liquid chromatography and the results obtained are set forth in Table I below:

TABLE I

| By-Products Components | Unpurified BPA By-Products Mixture (Wt. %) | Chroman-I Concentrate (Wt. %) |
| --- | --- | --- |
| BPA | 41.671 | 75.503 |
| o,p'-BPA | 13.073 | 1.143 |
| Cyclic IPP Dimer | 11.741 | 8.826 |
| Chroman-I | 7.082 | 13.505 |
| THP | 1.562 | 0.116 |
| IPP | 0.991 | — |
| Spiro Bi-Indane | 0.466 | 0.028 |
| Phenol | 1.626 | 0.012 |
| Uncalibrated Components | 21.788 | 0.867 |

As can be seen from the results in Table I above, the BPA content was increased about 80%, the chroman-I content was increased about 90%, and the cyclic IPP dimer content was decreased about 25%. The remaining components were either eliminated or substantially reduced to insignificant concentrations.

EXAMPLE 2

Alternate Method of Obtaining Chroman-I Concentrate

About 500 grams of unpurified BPA by-products were collected from a BPA manufacturing facility and placed in a vessel equipped with electrical heating tape wherein they were kept in a molten state at about 130° C.

To a 4-necked, round bottom flask equipped with a mechanical stirrer, water cooled condenser, dropping funnel, and heated by means of electrical tape, there was placed 500 grams of methylene chloride. To the well stirred methylene chloride solution, there was added the 500 grams of molten BPA by-products, the rate of addition of the molten by-products being used to control the reflux rate of the methylene chloride. The temperature of the solvent was 40° C. and had a dark color. After the addition of about half of the molten by-products, yellow colored crystals formed in the solution. Upon completing the addition of the molten by-products, the resultant thick, yellow mixture was cooled and filtered. The filter cake was washed with fresh methylene chloride to afford a white solid. The white, chroman-I concentrate filter cake was dried at 100° C. for 24 hours.

Using this method, the yields of chroman-I concentrate averaged about 96–150 grams which is equivalent to about 20–30% by weight of the unpurified, crude, BPA by-products.

EXAMPLE 3

Following the procedure of Example 1, additional lots of chroman-I concentrate were obtained from the 25 lb. lots of unpurified BPA by-products. These were also subjected to liquid chromatograph analyses from which a typical weight percent range of unpurified BPA by-products and chroman-I concentrate were obtained as shown in Table II below.

TABLE II

| By-Products Components | Unpurified BPA By-Products Mixture (Wt. %) Range | Average | Chroman-I Concentrate (Wt. %) Range | Average |
| --- | --- | --- | --- | --- |
| BPA | 4.00–95.00 | 50.00 | 70.00–80.00 | 75.00 |
| o,p'-BPA | 0.01–15.00 | 14.00 | 0.05–20.00 | 1.00 |
| Cyclic IPP Dimer | 0.01–15.00 | 14.00 | 6.00–10.00 | 8.00 |
| Chroman-I | 95.00–4.00 | 50.00 | 12.00–16.00 | 14.00 |
| THP | 0.01–2.00 | 1.50 | 1.00–0.50 | 1.00 |
| IPP | 0.01–15.00 | 0.10 | 6.00–10.00 | 0.01 |
| Spiro Bi-Indane | 0.01–0.50 | 0.35 | 0.08–0.50 | 0.30 |
| Phenol | 0.01–2.00 | 1.50 | 0.00–0.50 | 0.15 |
| Uncalibrated Components | 1.00–25.00 | 15.00 | 0.01–2.50 | 1.50 |

EXAMPLE 4

A high molecular weight aromatic polycarbonate resin was prepared employing the technique disclosed in U.S. Pat. 3,028,365 wherein phenol was employed as the chain stopper. The polycarbonate resin obtained in powdered form was then fed to an extruder operating at a temperature of about 500° F. to extrude the resin into strands and the extruded strands were chopped into pellets. The pellets were then injection molded at about 600° F. into test samples measuring about 3 in. × 2 in. × ⅛ in.

EXAMPLE 5

The same procedure was used as in Example 4 to obtain polycarbonate resin test samples except that the unpurified BPA by-products of Example 1 were used as the chain stopper in place of phenol.

EXAMPLE 6

The same procedure was followed as in Example 4 to obtain polycarbonate test samples except that the chroman-I concentrate of Example 1 was used as the chain stopper in place of phenol.

EXAMPLES 7 AND 8

The same procedures were followed as in Examples 4–6 except that prior to extruding the polycarbonate resins, they were each mixed with 9% by weight of the polycarbonate resin of a commercially obtained glass fiber by tumbling the ingredients together in a tumbler prior to extrusion.

The test samples of Examples 4–8 were subjected to physical tests to measure important physical properties. The results obtained are set forth in Table III below wherein the heat distortion temperatures under load (DTUL) were determined according to ASTM D-648, notched Izod (NI) impact results were obtained pursuant to ASTM D-256, intrinsic viscosity (IV) of the resins was determined by dissolving the resins in methylene chloride at 25° C., and the melt index (MI) of the resins was determined pursuant to modified ASTM D-1238.

TABLE III

Physical Properties of Polycarbonate Resins Obtained By Employing Different Chain Stoppers

| Sample of Example | DTUL at 264 psi (°F.) | NI (ft.lbs./in.) | IV (dl./g.) | MI |
|---|---|---|---|---|
| 4 | 269 | 16.3 | 0.51 | 7.26 |
| 5 | 276 | 1.3 | — | — |
| 6 | 283 | 16.3 | 0.53 | 6.87 |
| 7 | 288 | 2.9 | — | — |
| 8 | 302 | 3.6 | — | — |

The results in Table III above reveal that use of the chroman-I concentrate of the invention results in increasing heat distortion temperatures while maintaining or improving impact in test samples with and without glass fiber (Examples 6 and 8) as opposed to similar test samples obtained when phenol (Examples 4 and 7) and the mixture of unrefined BPA by-products (Example 5) were used as chain stoppers.

What is claimed is:

1. A process for obtaining a chroman-I concentrate from a mixture of BPA by-products, said process comprising
   slurrying a mixture of BPA by-products in a solvent system containing an inert, organic member until a solid is formed;
   collecting said resultant solid;
   washing said solid with said inert, organic member of said solvent system to form a white powder; and,
   drying said powder.

2. The process of claim 1 wherein said inert, organic member is selected from the group consisting of methylene chloride, chlorobenzene, cyclohexanone, carbon tetrachloride, and mixtures thereof.

3. The process of claim 2 wherein said inert, organic member is methylene chloride.

4. The process of claim 1 wherein the weight ratio of said BPA by-products to said inert, organic member is in the range of about 1:0.5–3.0.

5. The process of claim 4 wherein said weight ratio is about 1:1.

6. The process of claim 1 wherein said white powder consists essentially of BPA, cyclic IPP dimer and chroman-I.

7. A process for obtaining a chroman-I concentrate from a mixture of BPA by-products, said process comprising
   slurrying a mixture of BPA by-products in a solvent system containing an inert, organic member until a solid is formed, said mixture of by-products containing BPA, cyclic IPP dimer, chroman-I, THP, spiro bi-indane, phenol and o,p'-BPA, said inert organic member being selected from the group consisting of methylene chloride, chlorobenzene, cyclohexanone, carbon tetrachloride, and mixtures thereof, the weight ratio of said BPA by-products to said inert, organic member being in the range of about 1:0.5–3.0;
   collecting said resultant solid;
   washing said solid with said inert, organic member to form a white powder; and,
   drying said white powder which consists essentially of BPA, cyclic IPP dimer and chroman-I.

8. The process of claim 7 wherein said inert, organic member is methylene chloride.

9. The process of claim 7 wherein said weight ratio is about 1:1.

10. A process for obtaining a chroman-I concentrate from a mixture of BPA by-products, said process comprising
    charging a reactor vessel with a solvent system containing an inert organic member;
    adding to said solvent system a molten mixture of BPA by-products, the rate of addition of said molten by-products being sufficient to maintain said solvent system at constant reflux;
    upon completing the addition of said molten by-products, cooling and filtering the resultant mixture;
    washing the filter cake obtained with said inert organic member of said solvent system to form a white solid; and,
    drying said white filter cake solid.

11. The process of claim 10 wherein said inert organic member is selected from the group consisting of methylene chloride, chlorobenzene, cyclohexanone, carbon tetrachloride, and mixtures thereof.

12. The process of claim 11 wherein said inert organic member is methylene chloride.

13. The process of claim 10 wherein the weight ratio of said BPA by-products to said inert, organic member is in the range of about 1:0.5–3.0.

14. The process of claim 13 wherein said weight ratio is about 1:1.

15. The process of claim 10 wherein said white filter cake consists essentially of BPA, cyclic IPP dimer and chroman-I.

* * * * *